United States Patent
Burton

(10) Patent No.: US 8,921,317 B1
(45) Date of Patent: Dec. 30, 2014

(54) NANO-RECOMBINANT FIBRINOGEN FOR FIBRIN SEALANTS

(75) Inventor: Robert A. Burton, Columbia, MD (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 788 days.

(21) Appl. No.: 12/814,078

(22) Filed: Jun. 11, 2010

Related U.S. Application Data

(60) Provisional application No. 61/186,737, filed on Jun. 12, 2009.

(51) Int. Cl.
- *A61K 38/39* (2006.01)
- *A61K 47/48* (2006.01)
- *A61P 17/02* (2006.01)
- *C12Q 1/56* (2006.01)
- *C07K 1/04* (2006.01)
- *C07K 17/00* (2006.01)

(52) U.S. Cl.
USPC ............ 514/9.4; 514/9.3; 435/13; 530/381; 530/382

(58) Field of Classification Search
CPC ............................ C07K 14/75; A61K 38/363
USPC ............... 514/9.3, 9.4; 435/13; 530/381, 382
See application file for complete search history.

(56) References Cited

U.S. PATENT DOCUMENTS

| | | | |
|---|---|---|---|
| 5,330,974 A | 7/1994 | Pines et al. | |
| 5,464,471 A | 11/1995 | Whalen et al. | |
| 6,037,457 A | 3/2000 | Lord | |
| 6,552,172 B2 * | 4/2003 | Marx et al. | 530/382 |
| 6,908,899 B2 * | 6/2005 | Smith | 514/19.1 |
| 2007/0282247 A1 * | 12/2007 | Desai et al. | 604/19 |

OTHER PUBLICATIONS

Okumura et al., 2002, Blood, 99(10): 3654-3660.*
Zhang et al., 1996, Assembly and Secretion of Fibrinogen, The Journal of Biological Chemistry, 271(21): 12674-12680.*
Xu et al., 1996, The Assembly of Human Fibrinogen, The Journal of Biological Chemistry, 271(44): 27948-27953.*
Raman et al., "Structure-based design of peptides that self-assemble into regular polyhedral nanoparticles"; Nanomedicine: Nanotechnology, Biology, and Medicine 2 (2006); pp. 95-102 (Elsevier Publishing).
Park et al., "Preparation of silica nanoparticles: determination of the optimal synthesis conditions for small and uniform particles"; Colloids and Surfaces A: Physiochemical and Engineering Aspects 197 (2002); pp. 7-17 (Elsevier Publishing).
Bolyard, et al., "High-level expression of a functional human fibrinogen gamma chain in *Escherichia coli*"; Gene; vol. 66, No. 2 Jun. 30, 1988; Abstract only.
Bolyard, et al., "Expression in *Escherichia coli* of the Human Fibrinogen Bβ Chain and its Cleavage by Thrombin"; Blood, vol. 73 No. 5, Apr. 1989; pp. 1202-1206.

(Continued)

*Primary Examiner* — Amber D Steele
(74) *Attorney, Agent, or Firm* — Rossi, Kimms & McDowell

(57) ABSTRACT

A fibrin-based hemostatic agent suitable for both civilian and military use is disclosed. The hemostatic agent comprises (i) nanoparticles to which a plurality of Knob-A recognition sequences are attached, and (ii) coiled-coils of recombinantly-produced human fibrinogen α and chains and the γ chain globular domain. A delivery system for the hemostatic agent also is disclosed, which additionally comprises means for delivering (i) and (ii) to a wound site. The delivery means may be a $CO_2$ canister or a shaker jet.

17 Claims, 9 Drawing Sheets

Peptide Nanoparticle
- Self-assembling polyhedra of designed peptides conjugated to A-knobs replace the central E region of fibrinogen

Recombinant αγ-cc
- α and γ truncation mutants purified from *E. coli* and *P. pastoris* associate to form coiled-co

(56) References Cited

OTHER PUBLICATIONS

Roy, et al., "Assembly and Secretion of Recombinant Human Fibrinogen"; J. Biol. Chem., vol. 266 No. 8; Mar. 15, 1991; pp. 4758-4763.

Lord, et al., "Purification and characterization of recombinant human fibrinogen"; Blood Coagul Fibrinolysis, vol. 4 No. 1; Feb. 4, 1993; Abstract only.

Hartwig, et al., "Studies on the Assembly and Secretion of Fibrinogen"; J. Biol. Chem., vol. 266 No. 10; Apr. 5, 1991; pp. 6578-6585.

Roy et al., "Secretion of Biologically Active Recombinant Fibrinogen by Yeast"; J Biol Chem, vol. 270, No. 40; Oct. 6, 1995; pp. 23761-23767.

Butler et al., "Secretion of recombinant human fibrinogen by the murine mammary gland"; Transgenic Res, (5) Oct. 13, 2004; Abstract only.

Stephen Everse et al., "Crystal Structure of Fragment Double-D from Human Fibrin with Two Different Bound Ligands"; Biochemistry 1998, 37; pp. 8637-8642.

Doolittle et al., "Differences in Binding Specificity for the Homologous ç- and â-Chain "Holes" on Fibrinogen: Exclusive Binding of Ala-His-Arg-Pro-amide by the â-Chain Hole"; Biochemistry, 2006, vol. 45; pp. 13962-13969.

Lord et al., "Strategy for Recombinant Multichain Protein Synthesis: Fibrinogen Bâ-Chain Variants as Thrombin Substrates"; Biochemistry, 1996, vol. 35; pp. 2342-2348.

Kruse et al., "Mutant Fibrinogen Cleared from the Endoplasmic Reticulum via Endoplasmic Reticulum-Associated Protein Degradation and Autophagy"; American Journal of Pathology, vol. 168 No. 4, Apr. 2006; pp. 1299-1308.

* cited by examiner

Peptide Nanoparticle
- Self-assembling polyhedra of designed peptides conjugated to A-knobs replace the central E region of fibrinogen

Recombinant αγ-cc
- α and γ truncation mutants purified from *E. coli* and *P. pastoris* associate to form coiled-coils in the absence of the β chain.

Self Assembled Nano-recombinant Protofibril
- Preservation of physiologically relevant structure and protein binding sites yields unique advantage to cost, versatility, stability, and mitigates pathogen contamination risk.

```
ttt gga cat ctg tct cct act ggc aca gaa ttt tgg ctg gga aat gag aag att cat
 F   G   H   L   S   P   T   G   T   E   F   W   L   G   N   E   K   I   H ttg ata agc aca cag tct gcc atc cca tat gca tta aga gtg gga ctg gaa gac tgg aat
 L   I   S   T   Q   S   A   I   P   Y   A   L   R   V   G   L   E   D   W   N ggc aga acc agt act gca gac ttc aag atg ttc gtt gga cct gaa gct gac aag tac
 G   R   T   S   T   A   D   F   K   M   F   V   G   P   E   A   D   K   Y cgc cta aca tat gcc tac ttc gct ggt gat gct gat ggc ttt gat
 R   L   T   Y   A   Y   F   A   G   D   A   D   G   F   D ttt ggc gat agt cct aag gac aag ttt gcc ggc ttg cag gga tct ggt
 F   G   D   S   P   K   D   K   F   A   G   L   Q   G   S   G tgg gac aat gat cac aag tgt gaa aat cat cag tac tat gat act ggc
 W   D   N   D   H   K   C   E   N   H   Q   Y   Y   D   T   G tgg atg aac aag tgt gct ctc ggt ggc gct tat gtt att tgg caa gcc
 W   M   N   K   C   A   L   G   G   A   Y   V   I   W   Q   A tca aaa gca tct cct tat cac gat aat ata atc cca ttc aac aga act
 S   K   A   S   P   Y   H   D   N   I   I   P   F   N   R   T cgg tgg tat tcc atg aag act atg gga acc atg aag ata cca ttc aga ctc aca att
 R   W   Y   S   M   K   T   M   G   T   M   K   I   P   F   R   L   T   I gga gaa gga cag caa ggg gga gcc aaa cag gct gga gac gtt taa
 G   E   G   Q   Q   G   G   A   K   Q   A   G   D   V   stop
```

Fibrinogen Sticky-end PCR Primers for pGEX-6p-1
Aα Chain from C45 to Q221

N-Term GST Tag BamHI - XhoI

1. Forward - 5' gga tcc tgc cct tct ggc tgc agg atg aaa ggg ttg 3'   (SEQ ID NO: 8)
                G   S   C   P   S   G   C   R   M   K   G   L        (SEQ ID NO: 9)
                     ↑
              BamHI site    Fibrinogen Aα start 2. Reverse - 5' ctc gag tta ctg gct ctt aaa att tcc ggg aac caa 3'   (SEQ ID NO: 10)
                STP Q   S   K   F   N   G   P   V   L                (SEQ ID NO: 11)
                     ↑
              XhoI site    Fibrinogen Aα term 3. Forward - 5' gga tcc tgc cct tct ggc tgc agg atg aaa ggg ttg 3'   (SEQ ID NO: 12)
                G   S   C   P   S   G   C   R   M   K   G   L        (SEQ ID NO: 13)
                     ↑
              BamHI site    Fibrinogen Aα start 4. Reverse - 5' ctc gag tta ctg gct ctt aaa att tcc ggg aac caa 3'   (SEQ ID NO: 14)
                STP Q   S   K   F   N   G   P   V   L                (SEQ ID NO: 15)
                     ↑
              XhoI site    Fibrinogen Aα term

FIGURE 6

γChain from C45 to V437

N-Term GST Tag

1. Forward – 5' gga tcc tgt cca act acc tgt ggc att gca gat ttc 3' (SEQ ID NOS 16)
                 G   S   C   P   T   T   C   G   I   A   D   F      (SEQ ID NOS 17)
                 ⎱_____⎰
                 BamHI Site   Fibrinogen γ start 2. Reverse – 5' ctc gag tta aac gtc tcc agc ctg ttt ggc tcc ccc 3' (SEQ ID NOS 18)
                 STP V   D   G   A   Q   K   A   G   G              (SEQ ID NOS 19)
                 ⎱___⎰        ←
                 XhoI Site    Fibrinogen γ term 3. Forward – 5' gga tcc tgt cca act acc tgt ggc att gca gat ttc 3' (SEQ ID NOS 20)
                 G   S   C   P   T   T   C   G   I   A   D   F      (SEQ ID NOS 21)
                 ⎱_____⎰
                 BamHI Site   Fibrinogen γ start 4. Reverse – 5' ctc gag tta aac gtc tcc agc ctg ttt ggc tcc ccc 3' (SEQ ID NOS 22)
                 STP V   D   G   A   Q   K   A   G   G              (SEQ ID NOS 23)
                 ⎱___⎰        ←
                 XhoI Site    Fibrinogen γ term

FIGURE 7

NANO-RECOMBINANT FIBRINOGEN FOR FIBRIN SEALANTS

SEQUENCE LISTING

The instant application contains a Sequence Listing which has been submitted in ASCII format via EFS-Web and is hereby incorporated by reference in its entirety. Said ASCII copy, created on Sep. 3, 2010, is named 20070102.txt and is 24,419 bytes in size.

BACKGROUND OF THE INVENTION

A. Field of the Invention

The invention relates generally to a fibrin-based hemostatic agent suitable for both civilian and military use.

B. Description of the Related Art

Fibrinogen is a soluble protein found in the blood plasma of all vertebrates. When fibrinogen is acted upon by thrombin, a protein enzyme, it is converted into fibrin monomer. The coagulation cascade, of which fibrinogen is a central component, is the physiological response to wounds and vascular insult. It is effective for treatment of hemorrhage, burns, skin grafts, spinal injuries and cartilage repair.

Therapeutic compositions of naturally-derived fibrin sealants and agents contain human fibrinogen derived, or pooled, from multiple human donors, have been disclosed. Tissue adhesive preparations of this type usually consist of a fibrinogen solution containing Factor XIII, some additional proteins, such as fibronectin and albumin, and active or nonactive additions. A thrombin solution, which may contain calcium ions, typically is provided, or the preparation may rely on thrombin provided from the tissue area to be bonded itself. These solutions are commercially available in the form of either deep-frozen solutions or lyophilisate due to their lack of stability as liquid aqueous solutions. The products typically are packaged in the form of kits, which include the protein ingredients, means to prepare the solutions, and means to utilize the solutions.

Although medically superior in certain aspects, the overall use of fibrin has been limited due to several shortcomings. Because of the risk of viral disease such as HIV, hepatitis B and C, and BSE (bovine preparations), these compositions cannot safely be used as wound dressings, without preparation to remove pathogen contamination. Furthermore, the naturally-derived product has a naturally slow cascade, and it also is unstable in response to environmental factors such as heat and shock. Fibrin-based clotting systems are donor dependent and expensive, and entail a difficult thrombin-based activation, which requires a double barrel syringe and refrigerated storage.

One proposed solution to the risks characteristic of therapeutic products derived from human plasma is the use of fibrinogen from a mammalian source other than humans. However, non-human fibrinogen can result in a severe immune response. Even highly purified bovine fibrinogen compositions which are currently available, such as those described in U.S. Pat. No. 5,330,974, still contain some foreign antigen. Moreover, while these products avoid the risks of human pathogens, they still are expensive and do not solve the stability or ease of use considerations that are characteristic of the human-derived products.

U.S. Pat. No. 5,464,471 describes an improvement in the design of fibrin tissue adhesives which eliminates solution preparation and mixing time as well as the risk of viral transmission and severe immunologic response. The tissue adhesive uses genetically engineered fibrin monomers rather than fibrinogen to avoid the time and constraints of preparing and pre-mixing ingredients, as well as any risk of viral transmission. It is stated that this allows the product to be lyophilized from a single solution containing all of its constituents, including thrombin. Consequently, the agent is available as a dry powder which is activated upon blood contact producing effective hemostasis and subsequent adhesion.

Various synthetic pressure dressings have been designed that can clot severe bleeding within seconds of being applied. These dressings include QuikClot®, which is made with inorganic zeolite granules. In use, it forms a molecular sieve that traps molecules in a molecular "cage" and holds the trapped species by forming hydrogen bonds. The bond formation generates heat, and can produce secondary burns. This has been a drawback in the QuikClot® product. Newer versions of the product are partially prehydrated sponges and generate less heat, but have a slower clotting speed.

Another pressure dressing is HemCon®, which is made with chitosan (an extract from shrimp shells). HemCon® does not cause secondary burn injuries and is easier to remove than the granular form of QC. However, it is more expensive than QuikClot® and is not a natural component of the coagulation cascade.

Current methods and materials do not provide adequate emergency combat care to staunch blood flow and restore hemostasis. The need exists for a fibrin-based, rapid clot, thermally stable, easily applicable hemostatic agent that is sufficiently cost effective to be deployed with each and every war fighter in the field. Furthermore, a need exists for a technology that is applicable for both intra- and extracorporeal use, and that has several platforms of use, such as powders, sponges, sealants, films, foams, and bandages. The present invention satisfies these needs.

SUMMARY OF THE INVENTION

The present invention provides a hemostatic agent comprising (i) nanoparticles to which a plurality of Knob-A recognition sequences are attached, and (ii) recombinantly-produced human fibrinogen $\alpha$ and $\gamma$ chains, including coiled-coil domains of the $\alpha$ and $\gamma$ chains and the $\gamma$ chain globular domain.

The nanoparticles may be gold nanoparticles, silanized silica nanoparticles, or peptide nanoparticles.

The Knob-A recognition sequence comprises an $NH_2$-terminal Glycine-Proline-Arginine sequence. Preferably the Knob-A recognition sequence comprises a tail comprising one or both of Gly and Ser residues. The tail may comprises a tail of contiguous amino acids from the Act sequence that results when FpA is cleaved from the Act chain, and more particularly the Knob-A recognition sequence is GPRVVERHQSAC (SEQ ID NO: 1). It is the carboxyl terminus of the tail that is conjugated to the nanoparticles.

The recombinantly-produced human fibrinogen $\alpha$ and $\gamma$ chains comprise one or both of a truncation mutant of the $\alpha$ chain and a truncation mutant of the $\gamma$ chain, and in one embodiment comprises both a truncation mutant of the $\alpha$ chain and a truncation mutant of the $\gamma$ chain, coupled with a Knob-A recognition sequence which comprises an $NH_2$-terminal Glycine-Proline-Arginine sequence and is preferably GPRVVERHQSAC (SEQ ID NO: 1).

The present invention also provides a delivery system for a hemostatic agent, comprising (i) nanoparticles to which a plurality of Knob-A recognition sequences are attached, (ii) recombinantly-produced human fibrinogen $\alpha$ and $\gamma$ chains, including coiled-coil domains of the $\alpha$ and $\gamma$ chains and the $\gamma$ chain globular domain and (iii) means for delivering (i) and (ii) to a wound site. Components (i) and (ii) are lyophilized independently and then mixed.

The delivery means for delivering (i) and (ii) can be a pressurized canister or a shaker jet. When a pressurized canister is used, the pressurized canister can use supercritical $CO_2$, and (i) and (ii) are lyophilized and dissolved in the supercritical $CO_2$. The delivery system is operable with one hand.

BRIEF DESCRIPTION OF THE DRAWINGS

The foregoing advantages and features of the invention will become apparent upon reference to the following detailed description and the accompanying drawings, of which:

FIG. 2 is a diagram of nano-recombinant fibrin sealant in which Knob-A sequences attached to peptide nanoparticles function as the Nano-E component.

FIG. 4 shows the nucleotide (SEQ ID NO: 4) and protein (SEQ ID NO: 5) sequence of the α chain of fibrinogen.

FIGS. 5A and 5B show the nucleotide (SEQ ID NO: 6) and protein (SEQ ID NO: 7) sequence of the γ chain of fibrinogen.

FIG. 6 shows the PCR primers for the α chain of fibrinogen SEQ ID NOS 8-15, respectively, in order of appearance).

FIG. 7 shows the PCR primers for the γ chain of fibrinogen (SEQ ID NOS 16-23, respectively, in order of appearance).

DETAILED DESCRIPTION OF SPECIFIC EMBODIMENTS

Figure 1:
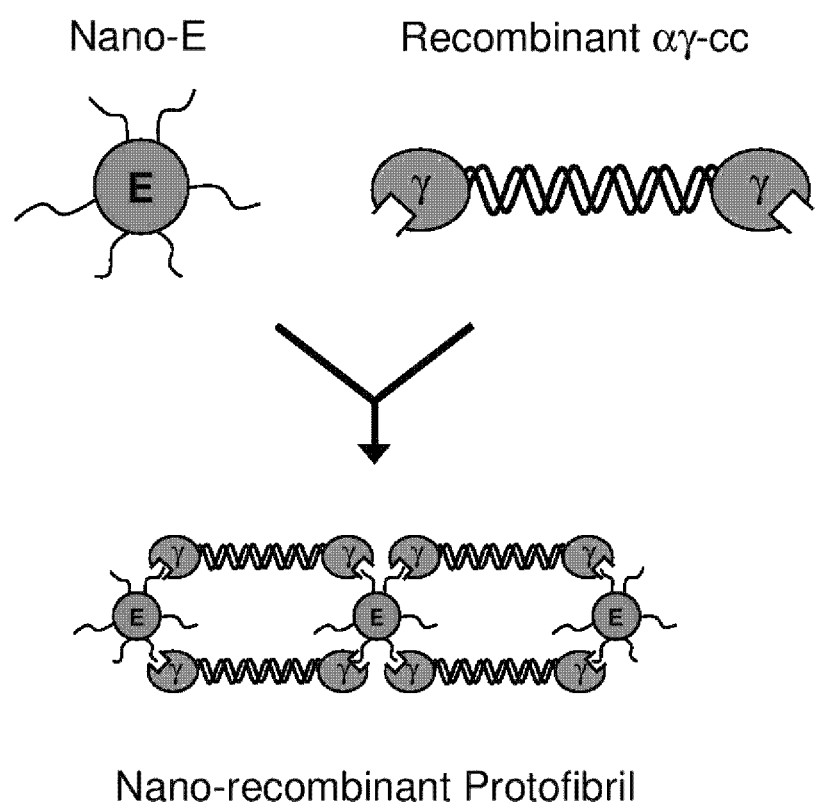
FIG. 1 is a diagram of nano-recombinant fibrin sealant in which Knob-A sequences attached to gold nanoparticles function as the Nano-E component.

A nano-recombinant fibrin sealant according to the invention provides a treatment for hemostasis that is both medically and economically viable, and that is suitable for use in first-responder environments where stability of other fibrin-based sealants are compromised, such as in field operations in the military. The sealant mimics and utilizes the advantages of the physiological coagulation cascade, while solving problems associated with previous hemostatic agents, including high cost, pathogen contamination and stability.

The sealant, according to the invention, uses recombinantly-produced fibrinogen molecules. Fibrinogen is a soluble plasma protein which consists of two identical disulfide-linked subunits, each of which is formed by three non-identical polypeptide chains, Aα, Bβ and γ. The $NH_2$-terminal portions of all six chains form the central E region of the molecule while their COOH-terminal portions form two identical distal D regions and two aC-domains. The molecule is linked by 29 disulfide bonds, 11 of which are in the central E region. The Aα and Bβ chains start with the 16-residue fibrinopeptide A and the 14-residue fibrinopeptide B sequence (fpA and fpB), respectively.

Fibrinogen participates in both the cellular phase and the fluid phase of coagulation. In the cellular phase, fibrinogen mediates platelet aggregation and fibrin supports clot retraction. In the fluid phase, fibrinogen is converted to fibrin in a reaction catalyzed by thrombin. Thrombin-mediated conversion of the plasma protein fibrinogen to the insoluble fibrin matrix is the major event in blood clotting. Proteolytic thrombin removal of fibrinopeptides A (FpA) and B (FpB) from the amino-termini of the Aα and Bβ chains, respectively, exposes in each E region two pairs of polymerization sites, or "knobs", denoted "Knob-A" and "Knob-B" starting with the Gly-Pro-Arg and Gly-His-Arg sequences, respectively, and produces fibrin monomers.

```
                                            (SEQ ID NO: 2)
      Thrombin cleavage site
1                    ↓
ADSGEGDFLAEGGGVR GPR VVERHQSAC KDSDWPFCSDED
      ↑           ↑
     FPA        KNOB-A
```

The interaction between these knobs and complementary polymerization sites, or holes, "a" and "b" located in the D regions of neighboring molecules (D:E:D interaction) results in spontaneous, yet ordered, polymerization of monomeric fibrin to the insoluble fibrin polymer. The exposed, centrally-located Gly-Pro-Arg- "knobs" fit into "holes" on the distally located γ-chain carboxyl domains (γC domains). Extension of the process leads to the formation of the intermediate protofibrils. FpA release initiates protofibril formation and FpB release enhances lateral aggregation. Fibrin polymers then are converted to insoluble fibers in a reaction catalyzed by FXIIIa, a transglutaminase that forms intermolecular amide bonds, crosslinking the fibrin monomers to form a clot.

The nano-recombinanat fibrin sealant employs a recombinant biomimetic fibrin clot approach. The design features a nanoparticle mimic of the fibrinogen E domain and a truncated αγ coiled-coil (αγ-cc). The approach circumvents the difficulty in expressing the central E region of fibrinogen recombinantly, by replacing it with a biomimetic "Knob A" tagged nanoparticle, a so-called Nano-E component, to which the γ globular domain binds in fibrin polymerization, as discussed herein.

The hemostatic agent according to the invention eliminates the need for either endogenous or exogenous thrombin. It does this by separately providing (i) the Knob-A sequences attached to nanoparticles, the so-called "Nano-E" component, and (ii) recombinantly-produced human fibrinogen α and γ chains, including coiled-coil domains of the α and γ chains and the γ chain globular domain.

The Knob-A recognition sequences can be attached to various nanoparticles to form the Nano-E component, as shown in FIGS. 1 and 2. Suitable nanoparticles include gold nanoparticles, silanized silica nanoparticles, and polyhedral nanoparticles of peptides that self-assemble into regular pentameric or trimeric coiled coil structures.

Preferred gold nanoparticles according to the invention are roughly spherical and about 5 nm in size, although other shapes and sizes, ranging from 5 to 50 nm can be used. They are commercially available, for example, from Nanocs Inc.) They can be produced in a liquid ("liquid chemical methods") by reduction of chloroauric acid ($H[AuCl_4]$), although more advanced and precise methods do exist. After dissolving $H[AuCl_4]$, the solution is rapidly stirred while a reducing agent is added. This causes $Au^{3+}$ ions to be reduced to neutral gold atoms. As more and more of these gold atoms form, the solution becomes supersaturated, and gold gradually starts to precipitate in the form of sub-nanometer particles. The rest of the gold atoms that form stick to the existing particles, and, if the solution is stirred vigorously enough, the particles will be fairly uniform in size. The nanoparticles themselves can come in a variety of shapes, including apheres, rods, cubes, and caps.

The Nano-E component can also be formed of peptide nanoparticles. The peptide nanoparticles are biocompatible biodegradable protein oligomerization domains and can be tagged on both the C- and N-termini with peptides. Thus, a peptide nanoparticle tagged with Knob A and a biomarker peptide, e.g., LKKTETQ (SEQ ID NO: 3), can serve as a nexus of protofibril formation at the wound surface.

Peptide nanoparticles are well-characterized pentameric and trimeric coiled-coil peptides that oligomerize to form stable non-immunogenic polyhedral nanoparticles. They are described in Raman et al., Nanomedicine: Nanotechnology, Biology, and Medicine 2 (2006) 95-102 (Elsevier Publishing), the contents of which are incorporated herein by reference in their entirety.

Silica nanoparticles are well-known in the field of electronics, where they are used to make substrates, insulators, etc. They are commercially available, for example, from Meliorum Technologies, Inc.), and can be prepared from tetramethylortho-silicate (TEOS) dissolved in ethanol by using a semi-batch process as described in Park et al., Colloids and Surfaces A: Physiochemical and Engineering Aspects 197 (2002) 7-17 (Elsevier Publishing), the contents of which are incorporated herein by reference in their entirety.

The Knob-A recognition sequence must, at a minimum, include the $NH_2$-terminal Knob-A recognition sequence of Glycine-Proline-Arginine (GPR). However, for steric and also for conjugation reasons relating to the conjugation of the Knob-A recognition sequence to the nanoparticles, the sequence which is attached to the nanoparticles preferably includes additional contiguous amino acids. Preferably these are from the Aα sequence that occurs naturally once FpA is cleaved from the Aα chain. However, any hydrophilic amino acid sequence can be used as long as both the GPR sequence and amino terminus are preserved. In this case, Gly or Ser residues are preferred because they are hydrophilic and small (providing flexibility). In one embodiment, the sequence that is attached to the nanoparticle is GPRVVERHQSAC (SEQ ID NO: 1).

The Knob-A recognition sequence is attached to the nanoparticles by its tail of amino acids using well know conjugation techniques. For example, the terminal cysteine residue in the sequence GPRVVERHQSAC (SEQ ID NO: 1) provides a convenient way of conjugating the sequence to the nanoparticle, using direct conjugation from the lone pair of electrons on the sulfur atom into the d-orbital of the gold atoms in the nanoparticle. Techniques using bis-functional linkers can be used in the case of the silica nanoparticles.

Figure 3:
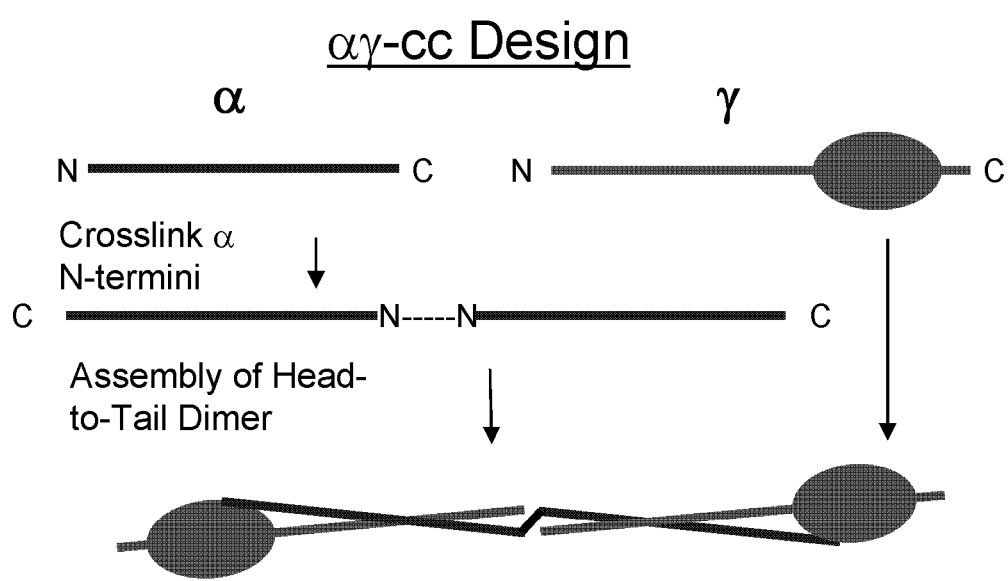
FIG. 3 is a diagram showing formation of the second component of the nano-recombinant fibrin sealant which includes the coiled-coil component.

The second major component in the nano-recombinant fibrin sealant comprise the α and γ chains, and more particularly those portions of the α and γ chains that form the coiled-coil component and the portion of the γ chain that forms the globular domain of the carboxy terminus, the latter comprising residues 151-411 of the γ chain. Thus, the second component includes all or part of the sequences of the α and γ chains of fibrinogen. The Aα and γ chains have been shown to form stable coiled-coils in the absence of the β chain, as shown diagrammatically in FIG. 3.

Each of the three chains of fibrinogen is coded by a separate gene, indicating that they are stable individual elements. These have been previously cloned, expressed, or assembled in mammalian and prokaryotic cell lines as full protein constructs or as site-directed and truncation mutants. See, for example, Bolyard, et al., *Gene*, 66:183, 1988, Bolyard, et al., *Blood*, 73(5):1202, 1989, Roy, et al., *J. Biol. Chem.*, 266(8): 4758, 1991, Lord, et al., *Blood Coagul Fibrinolysis*, 4(1):55, 1993, and Hartwig, et al., *J. Biol. Chem.*, 266(10):6578, 1991, the contents of each of these being incorporated herein by reference in their entirety.

Figure 4:
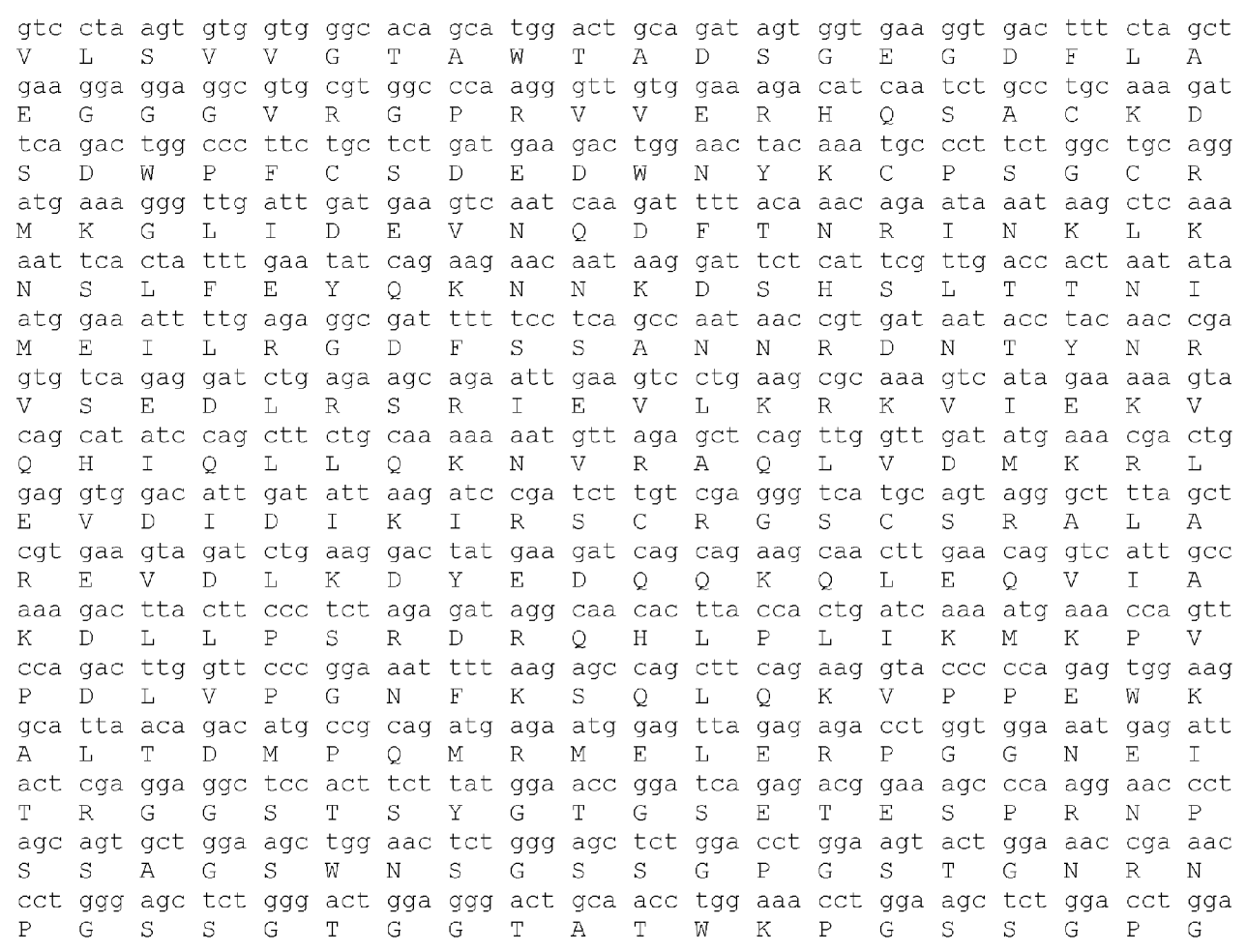
Figure 5A:
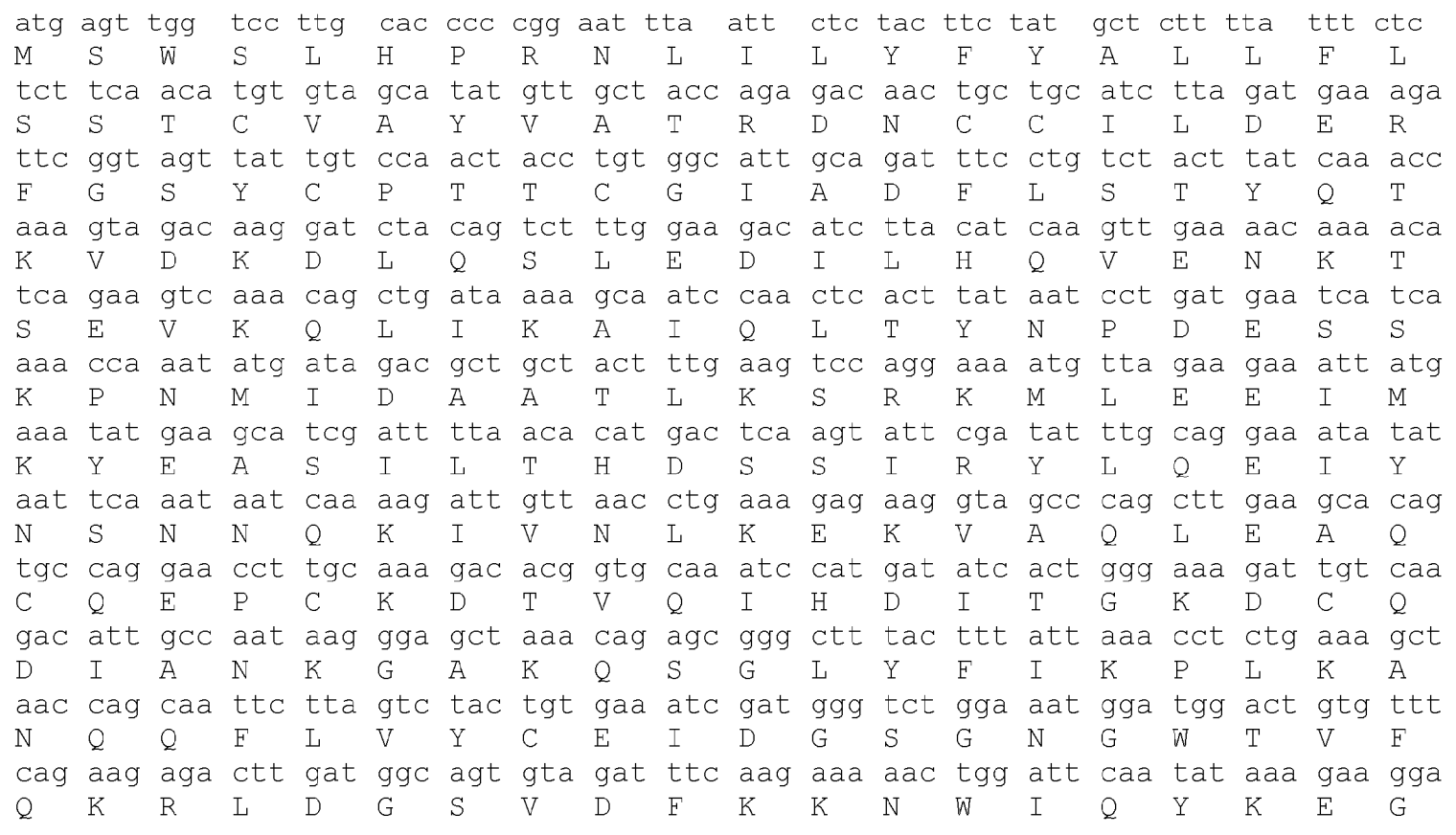

The sequences of the fibrinogen chains are available in public databases such as NCBI, GenBank and FASTA. Sequences for the α and γ chains are shown in FIG. 4 and FIGS. 5A and B, respectively. The entire α and γ chains may be used, or truncation mutants using only portions of the entire sequence of these chains can be used. Conservatively-modified variants of the full α and γ sequences, as well as of the truncation mutants, may be used as the second component.

The truncation mutants comprise all or part of the sequence of the α and γ chains, respectively, the only restriction on length and the portion of the sequence used being the ability to combine in the coiled-coil that is produced in natural fibrin and to include the globular domain of the carboxy terminus of the γ chain. A preferred alpha chain truncation mutant preferably is about 176 amino acids in length, and preferably includes amino acid residues 45-221. A preferred gamma chain truncation mutant preferably is about 392 amino acids in length, and preferably includes amino acid residues 45-437. Constructs which do not include the amino-terminal disulfide ring cysteine residues typically are less stable, but more easily purified and folded.

α and γ chain truncation mutants can be optimized for bacterial expression and then cloned and expressed. The sequences can be subcloned into pGEX plasmids (GE Healthcare) following standard molecular biology protocols such that product will be amino-terminally tagged with a cleavable glutathione S-transferase (GST) domain which can be used both for enhanced expression and purification, and for a chain $NH_3$-terminal dimerization. Other expression vectors may also be utilized providing alternate tags (e.g. pET vectors (Novagen) or ppic vectors (Invitrogen) in the case of *P. pastoris* yeast expression systems).

The α and γ sequences can be subcloned into separate plasmids which are expressed together in the same cells or separately in different cells, but typically the α and γ expression vectors are expressed separately in different cells which are cultured separately. Also, separate truncation mutants for the coiled-coil domain and the globular domain of the γ chain can be designed and subcloned into separate plasmids and expressed, but typically a single truncation mutant will comprise both the coiled-coil and globular domains of the γ chain.

*E. coli* expression tests can be conducted to determine conditions for optimal functional protein expression including: IPTG concentration, cell density, and induction length and temperature. Harvested cells can be lysed under pressure by Emulsiflex and the soluble fraction clarified by centrifugation. Analysis by PAGE is used to locate the target protein in either the cell pellet or supernatant. This fraction is purified by standard biochemical techniques utilizing a FPLC and glutathione and ion affinity chromatography under non-reducing conditions (DTT or TCEP). The purified a-constructs are $NH_3$-terminally linked and then mixed with the γ-constructs and dialyzed to form the αγ-cc (which includes the globular domain of the γ chain.

Fibrinogen assembles in a stepwise manner: α and γ associate preferentially and stably first, followed by incorporation of the β chain. As the A:α knob-hole interaction formed during protofibril formation is much stronger than the B:β (150-130 pN/interaction vs. 15-20 pN), and as the β chain is unnecessary for stable aγ association and function, nano-recombinant fibrinogen focuses on an α and γ coiled-coil construct (αγ-cc) with simultaneous protofibril and clot formation mediated by a Knob-A and biomarker target liganded nanoparticle (Nano-E).

While the Knob-A recognition sequences in particular are sufficiently short that they can be made by standard protein synthesis techniques, in preferred embodiments the α and γ chains are produced recombinantly. Prokaryotic, eukaryotic, or even transgenic, expression systems may be used to produce recombinant fibrin monomers for use in the hemostatic agent. Roy et al., *J Biol Chem*, 270(40): 23761-23767 (1995) have produced expression vectors for individual fibrinogen chain cDNAs and have used them to obtain functional fibrinogen molecules from yeast. U.S. Pat. No. 6,037,457 describes methods of producing recombinant fibrinogen in a long-term mammalian cell culture system. Butler et al., *Transgenic Res*, 13(5):437-50 (2004) have produced transgenic animals which secret both individual chains and assembled fibrinogen. The contents of these documents are incorporated herein by reference in their entirety.

In a preferred embodiment, prokaryotic expression and purification of truncated α and γ chains has been used. Careful peptide design incorporates the coiled-coil sections, protein interaction sites, and the γ globular domain that binds Knob-A. The α and γ chains have been shown to form stable coiled-coils in the absence of the β chain. Crosslinking of the α chain results in the formation of the final αγ coiled-coil construct.

Two possible approaches are GST fusion constructs and N-terminal crosslinking. In the former, expression of the α and γ chains as GST-fusion constructs allows for improved GSH affinity purification and N-terminal coupling via the tight dimerization of the GST modules. Alternatively, in the absence of a GST domain, the N-termini of the α peptides can be specifically crosslinked via a bis-carboxy linker under tight pH control or by enzymatic action.

GST is known to tightly dimerize, therefore it can be used as the α-chain amino-terminal linkage mechanism to generate the αγ-cc construct. With long segments, where the GST dimers are too large or otherwise hamper nano-recombinant fibrinogen protofibril and clot formation, chemical means can also be used to link the $NH_3$-α-chain termini. Bi-functional cross linker reagents such as bis-(sulfosuccinimidyl)suberate (BS3) or dimethyl adimimidate (DMA) can be used at a comparatively lower pH range (~5.5-6.5) so as to restrict or limit the cross-reaction with lysine side chain. Subsequent purification and assembly of the linked a-chains with the γ-chain and analysis by dynamic light scattering (DLS) and circular dichroism (CD) are used to verify the correct folding and association of αγ-cc.

In use, the Knob-A recognition sequences on the Nano-E component fit into their corresponding holes in the γ chains (or truncation mutant of the γ chain) of the second component, to produce a fibrin-like substance. The nanoparticles of the Nano-E component are like the knots in a net. FIGS. 1 and 2 show nano-recombinant fibrin sealants in which Knob-A sequences attached to gold nanoparticles or peptide nanoparticles, respectively, function as the Nano-E component. As shown, the exposed, centrally-located Gly-Pro-Arg- "knobs" fit into "holes" on the distally located γ-chain carboxyl domains (γC domains) of the coiled-coil component (described below). Extension of the process leads to the formation of the intermediate protofibrils.

In a first embodiment, the only fibrinogen sequences included in the hemostatic agent are the Knob-A recognition sequences attached to the nanoparticles, and the α and γ chain sequences, or portions thereof. The Aα and γ chains have been shown to form stable coiled-coils in the absence of the β chain, as shown diagrammatically in FIG. 3. However, in a further embodiment, the hemostatic agent additionally includes Knob-B recognition sequences attached to nanoparticles and Bβ chain sequences which correspond to those which occur naturally once FpB has been cleaved from the Bβ chain. Additional peptides may be attached to the nanoparticles and serve to direct particle association and fibrin clot formation selectively to the wounded site via wound associated biomarkers.

The recombinant Knob-A recognition sequences which are attached to the nanoparticles and the recombinant γ chains are physiologically-compatible and result in a fibrin-like substance. The term "physiologically compatible" means that the nanoparticles with the recombinant Knob-A recognition sequences, the recombinant γ chains, and the product that results when these two components combine are substantially non-immunogenic. The term "fibrin-like substance" means that the combination of the nanoparticles with the Knob-A recognition sequences and the γ chains produces a crosslinked matrix that functions like fibrin in providing hemostasis for wounds.

Figure 8C:
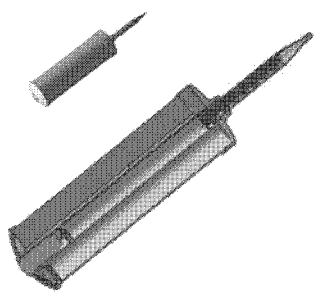
FIGS. 8A to 8C show the delivery system for the nano-recombinant fibrin sealant.
Figure 8B:
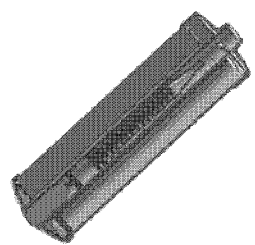
Figure 8A:

The two components in the nano-recombinant fibrin system are lyophilized independently and then mixed under inert conditions at appropriate ratios for optimal function with respect to clotting rates and mechanical performance. One suitable delivery system for the nano-recombinant fibrin sealant is shown in FIGS. 8A to 8C.

The mixture can be stored in small, lightweight pressurized canisters. In one approach, the lyophilized components are dissolved in supercritical $CO_2$. Supercritical $CO_2$ is an excellent solvent and does not typically irreversible denature dissolved protein samples. An inexpensive, lightweight design utilizes exchangeable $CO_2$ cartridges for rapid, easy dispersion, much like a $CO_2$ driven bicycle tire pump. Actuation of the trigger mechanism, releasing the pressure, disperses the lyophilized mixture, which will immediately begin to clot upon wound contact.

An alternative approach utilizes a shaker jet design. A calibrated orifice with shaking pentel design can be implemented to deliver the lyophilized powder to the wound directly.

With either approach, the system can be operated with one hand, and it is extremely portable. Both of these features make it particularly well-suited to military applications.

Fibrin glue or sealant applicators are based on a concept similar to that of epoxy applicators, which require separation of the components, proportional delivery of each component, and a static mixer nozzle. Assuming a minimum of 0.2 $m^2$ coverage at ~0.01 m thickness, ~400 ml of foaming agent are required. Based on a ClotFoam expansion coefficient of about 3-4 fold, 110 ml of liquid must be enclosed in the device and delivered. This volume greatly limits the design of the final device. Increasing the expansion coefficient 10 fold (40 ml pre-foam liquid) enables more design and manufacturing freedom while still meeting or exceeding the metrics, and results in a compact, single-hand operated "Instant Medic" applicator, which is shown in FIGS. 8A to 8C.

The Instant Medic applicator is cylindrical with approximately 150 cc displaced volume (φ3.9 cm×L 13 cm). Aluminum construction can be used for structural parts, providing a system mass of about 200 grams. It is designed to be operable by a single hand and uses a miniature cartridge of compressed $CO_2$ gas as the energy source. To operate, the user depresses a recessed button on one end of the cylinder—either using one's thumb or pushing into a hard object. This action punctures the $CO_2$ gas cylinder which releases high pressure (up to 850 psi) gas into the static mixer storage container. The piston top of the static mixer is then driven out of the storage chamber. To accomplish this, it must break through a "prestressed" polymer seal. When the static mixer has traveled the full length of the storage cylinder, ports in the side wall at the bottom of the storage chamber are exposed. This allows the gas pressure to transfer to the top side of the fluid displacement pistons. This pressure then forces the fluids out of the individual storage chambers (through a burst membrane), into the static mixer via side ports.

The static mixer is very similar to those used for mixing two part epoxies. The pistons are constructed of polymer with deep skirts. The deeps skirts serve two purposes; one is to increase the effective L/d of the piston and the other is to deform against the gas pressure to for a seal against the chamber wall. The piston also employs an elastomeric seal to prevent fluid mixing during storage.

The form of the nano-recombinant fibrin system is compatible with both intracavity and irregular surface wounds (0.2 m$^2$). In foam or spray form it molds to the target surface while clotting progresses. It binds specifically to damaged tissue, and key protein binding sites (plasmin, fibronectin, platelet binding, etc) are maintained in primary sequence. It enhances, and is eventually replaced by, the body's own physiologic response, at which point it easily can be removed.

A suitable protocol for plasmid construction and protein expression in *E. coli* and yeast is provided in the following example. PCR primers for the α and γ chains of fibrinogen are shown in FIGS. 6 and 7, respectively.

EXAMPLE

Preparation of Plates

About 10 ml of antibiotic in a 100 mg/ml concentration is prepared and kept at −20 C, wrapped in foil to protect it from light. LB agar is melted in a microwave, or LB and warm agar are mixed together to create a solution. The antibiotic is added to the warm LB agar mixture in a 0.1 ul:1 ml ratio. The agar is plated agar in Petri dishes and allowed to cool. The dishes are sealed with parafilm and stored upside down at +4 C.

Preparation of LB Medium

Sixteen capsules plus 9.5 mg of NaCl and 1 L of deionized water are combined to make 1 L of regular sodium LB. To make a lower sodium solution, 4.5 mg of NaCl are used instead of the 9.5 mg.

Transformation of Cells

The procedure outlined in the instruction paper included with the cells is followed. Eppendorf tubes are pre-chilled on ice, and LB medium is preheated to 42 C. Cells stored at −80 C are thawed on crushed ice, then gently mixed and aliquoted in 100 ul increments into the prechilled tubes. Beta-mercaptoethanol (1.7 ul) is added to each aliquot. The cells are incubated for 10 minutes on ice, swirling gently every two minutes.

Experimental DNA (0.1-50 ng) is added to all but one aliquot of cells. To the remaining aliquot, 1 ul of pUC is added as a control. The cells are Incubated on ice for 30 minutes. The tubes then are heat pulsed in a 42 C water bath for 45 seconds, and incubated on ice for 2 minutes.

Preheated LB medium (0.9 ml) at 42 C is added and the mixture is transferred to Falcon round bottom tubes. The tubes are Incubated at 37 C for one hour with shaking at 225-250 rpm. Less than 200 ul of transformation mixture is plated on LB agar plates with an appropriate antibiotic. For pUC, 2.5 ul is plated on an LB agar plate. The plates are incubated overnight at 37 C.

Preparation of cell stock

Ten ml of LB medium is placed in 50 ml Falcon round bottom tubes, and an appropriate amount of antibiotic is added. One colony of cells is picked from the Petri dish with the plastic tip of a pipette and placed in the LB medium, pipetting up and down to make sure all cells are in the medium. The tubes are placed in a shaker at 37 C for 14-16 hours.

After growth, 850 ul of cells are put into cryogenic vials and 150 ul of sterile glycerol is added to the vials with large pipette tips, to create 15% glycerol cell stock, and the vials are vortexed. The vials are stored at −80 C. The remaining solution is used in minipreps.

Miniprep DNA

The procedure outlined in the Invitrogen PureLink Quick Plasmid Miniprep Kit instruction manual is followed. On to five ml of an overnight culture is pelleted, and all medium is thoroughly removed from the cell pellet. The pellet is completely resuspended in 250 ul of Resuspension Buffer with RNase A. No cell clumps should remain. Lysis Buffer (250 ul) is added to the cells, which are mixed gently by inverting the capped tube five times. The tube is Incubates for 5 minutes at room temperature. Precipitation buffer (350 ul) is added and mixed immediately by inverting the tube until the solution is homogeneous. For large pellets, vigorous shaking may be necessary. The mixture is centrifuged at ~12,000×g for 10 minutes at room temperature using a microcentrifuge to clarify the lysate from lysis debris.

The supernatant is loaded from above into a spin column, and the spin column is placed with supernatant into a 2 ml wash tube, and centrifuge at 12,000×g for 1 minute. The flow-through is discarded and the column is placed back in the wash tube. Wash Buffer (W10-500 ul) with ethanol is added to the column, and incubated for 1 minute at room temperature, then centrifuged at ~12,000×g for 1 minute. The flow-through is discarded and the column is placed back into the wash tube.

Wash Buffer (W9—700 ul) with ethanol is added to the column, and the column is centrifuged at ~12,000×g for 1 minute. The flow-through is discarded and the column is placed back in the wash tube and centrifuge at ~12,000×g for 1 minute to remove any residual Wash Buffer. The wash tube with the flow-through is discarded. The spin column is placed in a clean 1.5 ml recovery tube. Preheated TE Buffer (50 ul) is added to the center of the column, and the column is incubated for 1 minute at room temperature, then centrifuged at ~12,000×g for 2 minutes. The recovery tube contains the purified plasmid DNA, and the column is discarded.

PCR

The standard protocol is followed for operation of the Eppendorf MasterCycler EP, using GE Healthcare's illustra PuReTaq Ready-To-Go PCR beads.

Digestion

Ultra-filtered water, thawed BSA (if needed), thawed NE Buffer, vector, and enzymes are combined, in order, to a total amount of 40 ul in an eppendorf tube. The digestion reaction is allowed to run while floating for two hours in a 37 C water bath.

Electrophoresis Gel

The procedure outlined in included Invitrogen E-Gel CloneWell Agarose Gels instruction manual is followed. The gel is removed from the package and inserted (with the comb in place) into the base by sliding the gel into the two electrode connections on the iBase, making certain that the two electrodes on the right side of the cassette are in contact with the two contacts on the iBase. The gel is pre-run (with the comb in place) using the program PRE-RUN 2 min. At the end of the pre-run, the current automatically shuts off. The combs are removed, and 20-25 ul prepared sample are loaded into well 1-8 of the top row. 5-10 ul DNA Molecular Weight Marker is loaded into the small middle well of the top row (marked M). 25 ul water is loaded into any remaining empty wells in the top row.

25-30 ul water is loaded into wells 1-8 of the bottom row, and 5-10 ul water in the middle well of the bottom row. The E-Gel iBase Power System is placed over a blue light transilluminator, the Run CloneWell program is selected, and the estimated Run time to Reference Line is selected as listed in the manual. The gel is monitored during the run, and stopped when the band of interest reaches the reference line.

At the end of the run, the iBase stops after the entered run time. If the band of interest does not reach the reference line, the gel is run until the band reaches the line. Once the band reaches the reference line, the bottom row is refilled with sterile water until the well is full. The gel is run for the time listed in the manual until the band enters the collection well. The DNA is collected from the well using a pipette, being careful not to perforate the agarose bottom of the collection well. Some residual DNA remains visible underneath the well due to migration in the agarose bottom. The collected DNA may be used without any further purification, additional DNA bands may be collected from the same well.

Ligation

Ready-To-Go T4 DNA Ligase Tubes are vortexed and then centrifuged to pellet the mix. The PCR product is added and digested vectors in varying ratios to ensure that the majority of vectors are inserted with PCR product, keeping the total liquid in the tube to 20 ul, and adding ultra-filtered water if needed. The tubes are incubated at room temperature for 3-5 minutes then gently mixed by pipetting and centrifuged briefly. The tubes are incubatec at 16 C for 30-45 minutes. 2 ul of the ligation reaction is used to transform 50 ul of competent cells.

Protein Induction

Transformed protein (BL21 DE3 pLysS) cells are grown overnight in 10 ml of LB with 1:1000 dilutions of appropriate antibiotics. Flasks of LB are autoclaved and 1:1000 dilutions of appropriate antibiotics are added. One ml of overnight growth is added to each cooled-down flask and shaken at 200-225 rpm and 37 C until the solution reaches an OD of 0.6 on the Nanodrop "cell culture" setting. At OD of 0.6, the cells are induced with 1:1000 dilution of thawed IPTG, and continue to shake for 3-8 hours. After induction, cells the cells are centrifuged at 6000×g for 10 minutes to pellet the cells, the supernatant is removed, and the cells are frozen at −20 C until ready to use.

Protein Lysing

Induced protein cells are resuspended in appropriate buffer solution with protease inhibitors, then rinsed with Emulsiflex with dd H2O and then buffer three times. The lysate is centrifuged for 30 minutes at 12,000×g, and Emulsiflex is removed with dd H2O and then 70% EtOH. The protein is stored in 70% EtOH.

FPLC

The "pump wash purifier" is run and then the whole system with filtered dd $H_2O$. The "pump wash purifier" is run and then the whole system with A1 line in the appropriate buffer. The program is run program, followed by washing with filtered dd $H_2O$, and then with 95% EtOH, and stored in 95% EtOH.

Protein Electrophoresis Gel

The standard protocol of operation as outlined in included instructions with the pre-made gels is followed, and they are stored in a refrigerator.

Thus, a nano-recombinant fibrinogen for fibrin sealants has been described according to the present invention. Many modifications and variations may be made to the techniques and structures described and illustrated herein without departing from the spirit and scope of the invention. Accordingly, it should be understood that the methods and devices described herein are illustrative only and are not limiting upon the scope of the invention.

This application is based on and claims priority to U.S. Provisional Patent Application 61/186,737, filed on Jun. 12, 2009. The disclosure of the priority application in its entirety, including the drawings, claims, and the specification thereof, is incorporated herein by reference.

What is claimed is:

1. A hemostatic agent comprising:
   (i) nanoparticles to which a plurality of fibrinogen Knob-A recognition sequences are attached, each fibrinogen Knob-A recognition sequence comprising
      (a) an NH$_2$-terminal Glycine-Proline-Arginine knob which fits into a hole on γC domains of fibrinogen and
      (b) a hydrophilic tail of contiguous amino acids, the carboxy terminus of which is attached to the nanoparticles, and
   (ii) separately provided recombinantly-produced human fibrinogen α and γ chains including coiled-coil domains of the α and γ chains and the γ chain globular domain.

2. A hemostatic agent according to claim 1, wherein said nanoparticles are gold nanoparticles.

3. A hemostatic agent according to claim 1, wherein said nanoparticles are silanized silica nanoparticles.

4. A hemostatic agent according to claim 1, wherein said nanoparticles are peptide nanoparticles.

5. A hemostatic agent according to claim 1, wherein said hydrophilic tail comprises one or both of Gly and Ser residues.

6. A hemostatic agent according to claim 1, wherein said hydrophilic tail of contiguous amino acids is from the Aα sequence that results when fibrinopeptide A is cleaved from the Aα chain.

7. A hemostatic agent according to claim 1, wherein said fibrinogen Knob-A recognition sequence comprises GPRVVERHQSAC (SEQ ID NO: 1).

8. A hemostatic agent according to claim 1, wherein said recombinantly-produced human fibrinogen α and γ chains are a truncation mutant of the α chain and a truncation mutant of the γ chain, said truncation mutant retaining the ability to combine in the coiled-coil that is produced in natural fibrin and including the globular domain of the carboxy terminus of the γ chain.

9. A hemostatic agent according to claim 1, wherein said recombinantly-produced human fibrinogen α and γ chains are one or both of a truncation mutant of the α chain and a truncation mutant of the γ chain, said truncation mutant retaining the ability to combine in the coiled-coil that is produced in natural fibrin and including the globular domain of the carboxy terminus of the γ chain.

10. A hemostatic agent according to claim 9, wherein said truncation mutant does not include amino-terminal disulfide ring cysteine residues.

11. A hemostatic agent according to claim 9, wherein said truncation mutant includes amino-terminal disulfide ring cysteine residues.

12. A hemostatic agent according to claim 1, wherein said recombinantly-produced human fibrinogen α chain is a truncation mutant of the α chain, said truncation mutant retaining the ability to combine in the coiled-coil that is produced in natural fibrin and including the globular domain of the carboxy terminus of the γ chain.

13. A hemostatic agent according to claim 12, wherein said α chain truncation mutant is about 176 amino acids in length.

14. A hemostatic agent according to claim 12, wherein said α chain truncation mutant includes amino acid residues 45-221 of SEQ ID NO: 5.

15. A hemostatic agent according to claim 1, wherein said recombinantly-produced human fibrinogen γ chain is a truncation mutant of the γ chain, said truncation mutant retaining the ability to combine in the coiled-coil that is produced in natural fibrin and including the globular domain of the carboxy terminus of the γ chain.

16. A hemostatic agent according to claim 15, wherein said γ chain truncation mutant is about 392 amino acids in length.

17. A hemostatic agent according to claim 15, wherein said γ chain truncation mutant includes amino acid residues 45-437 of SEQ ID NO: 7.

* * * * *

SEQUENCE LISTING

```
<160> NUMBER OF SEQ ID NOS: 23

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Pro Arg Val Val Glu Arg His Gln Ser Ala Cys
1               5                   10

<210> SEQ ID NO 2
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Asp Ser Gly Glu Gly Asp Phe Leu Ala Glu Gly Gly Gly Val Arg
1               5                   10                  15
```

```
Gly Pro Arg Val Val Glu Arg His Gln Ser Ala Cys Lys Asp Ser Asp
            20                  25                  30

Trp Pro Phe Cys Ser Asp Glu Asp
        35                  40

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Lys Lys Thr Glu Thr Gln
1               5

<210> SEQ ID NO 4
<211> LENGTH: 960
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(960)

<400> SEQUENCE: 4 gtc cta agt gtg gtg ggc aca gca tgg act gca gat agt ggt gaa ggt      48
Val Leu Ser Val Val Gly Thr Ala Trp Thr Ala Asp Ser Gly Glu Gly
1               5                   10                  15 gac ttt cta gct gaa gga gga ggc gtg cgt ggc cca agg gtt gtg gaa      96
Asp Phe Leu Ala Glu Gly Gly Gly Val Arg Gly Pro Arg Val Val Glu
            20                  25                  30 aga cat caa tct gcc tgc aaa gat tca gac tgg ccc ttc tgc tct gat     144
Arg His Gln Ser Ala Cys Lys Asp Ser Asp Trp Pro Phe Cys Ser Asp
        35                  40                  45 gaa gac tgg aac tac aaa tgc cct tct ggc tgc agg atg aaa ggg ttg     192
Glu Asp Trp Asn Tyr Lys Cys Pro Ser Gly Cys Arg Met Lys Gly Leu
    50                  55                  60 att gat gaa gtc aat caa gat ttt aca aac aga ata aat aag ctc aaa     240
Ile Asp Glu Val Asn Gln Asp Phe Thr Asn Arg Ile Asn Lys Leu Lys
65                  70                  75                  80 aat tca cta ttt gaa tat cag aag aac aat aag gat tct cat tcg ttg     288
Asn Ser Leu Phe Glu Tyr Gln Lys Asn Asn Lys Asp Ser His Ser Leu
                85                  90                  95 acc act aat ata atg gaa att ttg aga ggc gat ttt tcc tca gcc aat     336
Thr Thr Asn Ile Met Glu Ile Leu Arg Gly Asp Phe Ser Ser Ala Asn
            100                 105                 110 aac cgt gat aat acc tac aac cga gtg tca gag gat ctg aga agc aga     384
Asn Arg Asp Asn Thr Tyr Asn Arg Val Ser Glu Asp Leu Arg Ser Arg
        115                 120                 125 att gaa gtc ctg aag cgc aaa gtc ata gaa aaa gta cag cat atc cag     432
Ile Glu Val Leu Lys Arg Lys Val Ile Glu Lys Val Gln His Ile Gln
    130                 135                 140 ctt ctg caa aaa aat gtt aga gct cag ttg gtt gat atg aaa cga ctg     480
Leu Leu Gln Lys Asn Val Arg Ala Gln Leu Val Asp Met Lys Arg Leu
145                 150                 155                 160 gag gtg gac att gat att aag atc cga tct tgt cga ggg tca tgc agt     528
Glu Val Asp Ile Asp Ile Lys Ile Arg Ser Cys Arg Gly Ser Cys Ser
                165                 170                 175
```

```
agg gct tta gct cgt gaa gta gat ctg aag gac tat gaa gat cag cag    576
Arg Ala Leu Ala Arg Glu Val Asp Leu Lys Asp Tyr Glu Asp Gln Gln
            180                 185                 190 aag caa ctt gaa cag gtc att gcc aaa gac tta ctt ccc tct aga gat    624
Lys Gln Leu Glu Gln Val Ile Ala Lys Asp Leu Leu Pro Ser Arg Asp
        195                 200                 205 agg caa cac tta cca ctg atc aaa atg aaa cca gtt cca gac ttg gtt    672
Arg Gln His Leu Pro Leu Ile Lys Met Lys Pro Val Pro Asp Leu Val
    210                 215                 220 ccc gga aat ttt aag agc cag ctt cag aag gta ccc cca gag tgg aag    720
Pro Gly Asn Phe Lys Ser Gln Leu Gln Lys Val Pro Pro Glu Trp Lys
225                 230                 235                 240 gca tta aca gac atg ccg cag atg aga atg gag tta gag aga cct ggt    768
Ala Leu Thr Asp Met Pro Gln Met Arg Met Glu Leu Glu Arg Pro Gly
                245                 250                 255 gga aat gag att act cga gga ggc tcc act tct tat gga acc gga tca    816
Gly Asn Glu Ile Thr Arg Gly Gly Ser Thr Ser Tyr Gly Thr Gly Ser
            260                 265                 270 gag acg gaa agc cca agg aac cct agc agt gct gga agc tgg aac tct    864
Glu Thr Glu Ser Pro Arg Asn Pro Ser Ser Ala Gly Ser Trp Asn Ser
        275                 280                 285 ggg agc tct gga cct gga agt act gga aac cga aac cct ggg agc tct    912
Gly Ser Ser Gly Pro Gly Ser Thr Gly Asn Arg Asn Pro Gly Ser Ser
    290                 295                 300 ggg act gga ggg act gca acc tgg aaa cct gga agc tct gga cct gga    960
Gly Thr Gly Gly Thr Ala Thr Trp Lys Pro Gly Ser Ser Gly Pro Gly
305                 310                 315                 320

<210> SEQ ID NO 5
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Val Leu Ser Val Val Gly Thr Ala Trp Thr Ala Asp Ser Gly Glu Gly
1               5                   10                  15

Asp Phe Leu Ala Glu Gly Gly Val Arg Gly Pro Arg Val Val Glu
            20                  25                  30

Arg His Gln Ser Ala Cys Lys Asp Ser Asp Trp Pro Phe Cys Ser Asp
        35                  40                  45

Glu Asp Trp Asn Tyr Lys Cys Pro Ser Gly Cys Arg Met Lys Gly Leu
    50                  55                  60

Ile Asp Glu Val Asn Gln Asp Phe Thr Asn Arg Ile Asn Lys Leu Lys
65                  70                  75                  80

Asn Ser Leu Phe Glu Tyr Gln Lys Asn Asn Lys Asp Ser His Ser Leu
                85                  90                  95

Thr Thr Asn Ile Met Glu Ile Leu Arg Gly Asp Phe Ser Ser Ala Asn
            100                 105                 110

Asn Arg Asp Asn Thr Tyr Asn Arg Val Ser Glu Asp Leu Arg Ser Arg
        115                 120                 125

Ile Glu Val Leu Lys Arg Lys Val Ile Glu Lys Val Gln His Ile Gln
    130                 135                 140

Leu Leu Gln Lys Asn Val Arg Ala Gln Leu Val Asp Met Lys Arg Leu
145                 150                 155                 160

Glu Val Asp Ile Asp Ile Lys Ile Arg Ser Cys Arg Gly Ser Cys Ser
                165                 170                 175
```

```
Arg Ala Leu Ala Arg Glu Val Asp Leu Lys Asp Tyr Glu Asp Gln Gln
            180                 185                 190

Lys Gln Leu Glu Gln Val Ile Ala Lys Asp Leu Leu Pro Ser Arg Asp
        195                 200                 205

Arg Gln His Leu Pro Leu Ile Lys Met Lys Pro Val Pro Asp Leu Val
    210                 215                 220

Pro Gly Asn Phe Lys Ser Gln Leu Gln Lys Val Pro Pro Glu Trp Lys
225                 230                 235                 240

Ala Leu Thr Asp Met Pro Gln Met Arg Met Glu Leu Glu Arg Pro Gly
                245                 250                 255

Gly Asn Glu Ile Thr Arg Gly Gly Ser Thr Ser Tyr Gly Thr Gly Ser
            260                 265                 270

Glu Thr Glu Ser Pro Arg Asn Pro Ser Ser Ala Gly Ser Trp Asn Ser
        275                 280                 285

Gly Ser Ser Gly Pro Gly Ser Thr Gly Asn Arg Asn Pro Gly Ser Ser
    290                 295                 300

Gly Thr Gly Gly Thr Ala Thr Trp Lys Pro Gly Ser Ser Gly Pro Gly
305                 310                 315                 320

<210> SEQ ID NO 6
<211> LENGTH: 1314
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1311)

<400> SEQUENCE: 6 atg agt tgg tcc ttg cac ccc cgg aat tta att ctc tac ttc tat gct      48
Met Ser Trp Ser Leu His Pro Arg Asn Leu Ile Leu Tyr Phe Tyr Ala
1               5                   10                  15 ctt tta ttt ctc tct tca aca tgt gta gca tat gtt gct acc aga gac      96
Leu Leu Phe Leu Ser Ser Thr Cys Val Ala Tyr Val Ala Thr Arg Asp
            20                  25                  30 aac tgc tgc atc tta gat gaa aga ttc ggt agt tat tgt cca act acc     144
Asn Cys Cys Ile Leu Asp Glu Arg Phe Gly Ser Tyr Cys Pro Thr Thr
        35                  40                  45 tgt ggc att gca gat ttc ctg tct act tat caa acc aaa gta gac aag     192
Cys Gly Ile Ala Asp Phe Leu Ser Thr Tyr Gln Thr Lys Val Asp Lys
    50                  55                  60 gat cta cag tct ttg gaa gac atc tta cat caa gtt gaa aac aaa aca     240
Asp Leu Gln Ser Leu Glu Asp Ile Leu His Gln Val Glu Asn Lys Thr
65                  70                  75                  80 tca gaa gtc aaa cag ctg ata aaa gca atc caa ctc act tat aat cct     288
Ser Glu Val Lys Gln Leu Ile Lys Ala Ile Gln Leu Thr Tyr Asn Pro
                85                  90                  95 gat gaa tca tca aaa cca aat atg ata gac gct gct act ttg aag tcc     336
Asp Glu Ser Ser Lys Pro Asn Met Ile Asp Ala Ala Thr Leu Lys Ser
            100                 105                 110 agg aaa atg tta gaa gaa att atg aaa tat gaa gca tcg att tta aca     384
Arg Lys Met Leu Glu Glu Ile Met Lys Tyr Glu Ala Ser Ile Leu Thr
        115                 120                 125 cat gac tca agt att cga tat ttg cag gaa ata tat aat tca aat aat     432
His Asp Ser Ser Ile Arg Tyr Leu Gln Glu Ile Tyr Asn Ser Asn Asn
    130                 135                 140
```

```
caa aag att gtt aac ctg aaa gag aag gta gcc cag ctt gaa gca cag      480
Gln Lys Ile Val Asn Leu Lys Glu Lys Val Ala Gln Leu Glu Ala Gln
145                 150                 155                 160 tgc cag gaa cct tgc aaa gac acg gtg caa atc cat gat atc act ggg      528
Cys Gln Glu Pro Cys Lys Asp Thr Val Gln Ile His Asp Ile Thr Gly
                165                 170                 175 aaa gat tgt caa gac att gcc aat aag gga gct aaa cag agc ggg ctt      576
Lys Asp Cys Gln Asp Ile Ala Asn Lys Gly Ala Lys Gln Ser Gly Leu
            180                 185                 190 tac ttt att aaa cct ctg aaa gct aac cag caa ttc tta gtc tac tgt      624
Tyr Phe Ile Lys Pro Leu Lys Ala Asn Gln Gln Phe Leu Val Tyr Cys
        195                 200                 205 gaa atc gat ggg tct gga aat gga tgg act gtg ttt cag aag aga ctt      672
Glu Ile Asp Gly Ser Gly Asn Gly Trp Thr Val Phe Gln Lys Arg Leu
    210                 215                 220 gat ggc agt gta gat ttc aag aaa aac tgg att caa tat aaa gaa gga      720
Asp Gly Ser Val Asp Phe Lys Lys Asn Trp Ile Gln Tyr Lys Glu Gly
225                 230                 235                 240 ttt gga cat ctg tct cct act ggc aca aca gaa ttt tgg ctg gga aat      768
Phe Gly His Leu Ser Pro Thr Gly Thr Thr Glu Phe Trp Leu Gly Asn
                245                 250                 255 gag aag att cat ttg ata agc aca cag tct gcc atc cca tat gca tta      816
Glu Lys Ile His Leu Ile Ser Thr Gln Ser Ala Ile Pro Tyr Ala Leu
            260                 265                 270 aga gtg gaa ctg gaa gac tgg aat ggc aga acc agt act gca gac tat      864
Arg Val Glu Leu Glu Asp Trp Asn Gly Arg Thr Ser Thr Ala Asp Tyr
        275                 280                 285 gcc atg ttc aag gtg gga cct gaa gct gac aag tac cgc cta aca tat      912
Ala Met Phe Lys Val Gly Pro Glu Ala Asp Lys Tyr Arg Leu Thr Tyr
    290                 295                 300 gcc tac ttc gct ggt ggg gat gct gga gat gcc ttt gat ggc ttt gat      960
Ala Tyr Phe Ala Gly Gly Asp Ala Gly Asp Ala Phe Asp Gly Phe Asp
305                 310                 315                 320 ttt ggc gat gat cct agt gac aag ttt ttc aca tcc cat aat ggc ttg     1008
Phe Gly Asp Asp Pro Ser Asp Lys Phe Phe Thr Ser His Asn Gly Leu
                325                 330                 335 cag ttc agt acc tgg gac aat gac aat gat aag ttt gaa ggc aac tgt     1056
Gln Phe Ser Thr Trp Asp Asn Asp Asn Asp Lys Phe Glu Gly Asn Cys
            340                 345                 350 gct gaa cag gat gga tct ggt tgg tgg atg aac aag tgt cac gct ggc     1104
Ala Glu Gln Asp Gly Ser Gly Trp Trp Met Asn Lys Cys His Ala Gly
        355                 360                 365 cat ctc aat gga gtt tat tac caa ggt ggc act tac tca aaa gca tct     1152
His Leu Asn Gly Val Tyr Tyr Gln Gly Gly Thr Tyr Ser Lys Ala Ser
    370                 375                 380 act cct aat ggt tat gat aat ggc att att tgg gcc act tgg aaa acc     1200
Thr Pro Asn Gly Tyr Asp Asn Gly Ile Ile Trp Ala Thr Trp Lys Thr
385                 390                 395                 400 cgg tgg tat tcc atg aag aaa acc act atg aag ata atc cca ttc aac     1248
Arg Trp Tyr Ser Met Lys Lys Thr Thr Met Lys Ile Ile Pro Phe Asn
                405                 410                 415 aga ctc aca att gga gaa gga cag caa cac cac ctg ggg gga gcc aaa     1296
Arg Leu Thr Ile Gly Glu Gly Gln Gln His His Leu Gly Gly Ala Lys
            420                 425                 430 cag gct gga gac gtt taa                                             1314
Gln Ala Gly Asp Val
        435

<210> SEQ ID NO 7
```

```
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

Met Ser Trp Ser Leu His Pro Arg Asn Leu Ile Leu Tyr Phe Tyr Ala
1               5                   10                  15

Leu Leu Phe Leu Ser Ser Thr Cys Val Ala Tyr Val Ala Thr Arg Asp
                20                  25                  30

Asn Cys Cys Ile Leu Asp Glu Arg Phe Gly Ser Tyr Cys Pro Thr Thr
            35                  40                  45

Cys Gly Ile Ala Asp Phe Leu Ser Thr Tyr Gln Thr Lys Val Asp Lys
        50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
            100                 105                 110

Arg Lys Met Leu Glu Glu Ile Met Lys Tyr Glu Ala Ser Ile Leu Thr
        115                 120                 125

His Asp Ser Ser Ile Arg Tyr Leu Gln Glu Ile Tyr Asn Ser Asn Asn
130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
        195                 200                 205

Glu Ile Asp Gly Ser Gly Asn Gly Trp Thr Val Phe Gln Lys Arg Leu
210                 215                 220

Asp Gly Ser Val Asp Phe Lys Lys Asn Trp Ile Gln Tyr Lys Glu Gly
225                 230                 235                 240

Phe Gly His Leu Ser Pro Thr Gly Thr Thr Glu Phe Trp Leu Gly Asn
                245                 250                 255

Glu Lys Ile His Leu Ile Ser Thr Gln Ser Ala Ile Pro Tyr Ala Leu
            260                 265                 270

Arg Val Glu Leu Glu Asp Trp Asn Gly Arg Thr Ser Thr Ala Asp Tyr
        275                 280                 285

Ala Met Phe Lys Val Gly Pro Glu Ala Asp Lys Tyr Arg Leu Thr Tyr
290                 295                 300

Ala Tyr Phe Ala Gly Gly Asp Ala Gly Asp Ala Phe Asp Gly Phe Asp
305                 310                 315                 320

Phe Gly Asp Asp Pro Ser Asp Lys Phe Phe Thr Ser His Asn Gly Leu
                325                 330                 335

Gln Phe Ser Thr Trp Asp Asn Asp Asn Asp Lys Phe Glu Gly Asn Cys
            340                 345                 350

Ala Glu Gln Asp Gly Ser Gly Trp Trp Met Asn Lys Cys His Ala Gly
        355                 360                 365

His Leu Asn Gly Val Tyr Tyr Gln Gly Gly Thr Tyr Ser Lys Ala Ser
            370                 375                 380

Thr Pro Asn Gly Tyr Asp Asn Gly Ile Ile Trp Ala Thr Trp Lys Thr
385                 390                 395                 400

Arg Trp Tyr Ser Met Lys Lys Thr Thr Met Lys Ile Ile Pro Phe Asn
                405                 410                 415

Arg Leu Thr Ile Gly Glu Gly Gln Gln His His Leu Gly Gly Ala Lys
            420                 425                 430

Gln Ala Gly Asp Val
        435

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (1)..(36)

<400> SEQUENCE: 8 gga tcc tgc cct tct ggc tgc agg atg aaa ggg ttg                    36
Gly Ser Cys Pro Ser Gly Cys Arg Met Lys Gly Leu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ser Cys Pro Ser Gly Cys Arg Met Lys Gly Leu
1               5                   10

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (10)..(36)

<400> SEQUENCE: 10 ctcgagtta ctg gct ctt aaa att tcc ggg aac caa                      36
          Gln Ser Lys Phe Asn Gly Pro Val Leu
            1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Ser Lys Phe Asn Gly Pro Val Leu
1               5

```
<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (1)..(36)

<400> SEQUENCE: 12 gga tcc tgc cct tct ggc tgc agg atg aaa ggg ttg                      36
Gly Ser Cys Pro Ser Gly Cys Arg Met Lys Gly Leu
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ser Cys Pro Ser Gly Cys Arg Met Lys Gly Leu
1               5                   10

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (10)..(36)

<400> SEQUENCE: 14 ctcgagtta ctg gct ctt aaa att tcc ggg aac caa                        36
          Gln Ser Lys Phe Asn Gly Pro Val Leu
              1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Ser Lys Phe Asn Gly Pro Val Leu
1               5

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (1)..(36)

<400> SEQUENCE: 16
```

```
gga tcc tgt cca act acc tgt ggc att gca gat ttc                    36
Gly Ser Cys Pro Thr Thr Cys Gly Ile Ala Asp Phe
1               5                   10
```

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Gly Ser Cys Pro Thr Thr Cys Gly Ile Ala Asp Phe
1               5                   10
```

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (10)..(36)

<400> SEQUENCE: 18

```
ctcgagtta aac gtc tcc agc ctg ttt ggc tcc ccc                      36
          Val Asp Gly Ala Gln Lys Ala Gly Gly
            1               5
```

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Val Asp Gly Ala Gln Lys Ala Gly Gly
1               5
```

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (1)..(36)

<400> SEQUENCE: 20

```
gga tcc tgt cca act acc tgt ggc att gca gat ttc                    36
Gly Ser Cys Pro Thr Thr Cys Gly Ile Ala Asp Phe
1               5                   10
```

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Gly Ser Cys Pro Thr Thr Cys Gly Ile Ala Asp Phe
1               5                   10

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: CDS
<222> LOCATION: (10)..(36)

<400> SEQUENCE: 22 ctcgagtta aac gtc tcc agc ctg ttt ggc tcc ccc                        36
          Val Asp Gly Ala Gln Lys Ala Gly Gly
          1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Asp Gly Ala Gln Lys Ala Gly Gly
1               5
```